United States Patent [19]

Di Giuliomaria et al.

[11] Patent Number: 4,757,822
[45] Date of Patent: Jul. 19, 1988

[54] INSTRUMENT TO DETECT AND REPRESENT THE CROSS-SECTIONAL VARIATIONS OF A BLOOD VESSEL

[75] Inventors: Claudio Di Giuliomaria; Romeo Sacco; Luca di Marzo, all of Rome, Italy

[73] Assignee: Biotronix S.R.L., Italy

[21] Appl. No.: 821,612

[22] Filed: Jan. 23, 1986

[30] Foreign Application Priority Data

Feb. 7, 1985 [IT] Italy ............................ 47653 A/85

[51] Int. Cl.$^4$ ............................................ A61B 10/00
[52] U.S. Cl. .................................................. 128/663
[58] Field of Search ............................... 128/660–663, 128/699, 210; 340/743

[56] References Cited

U.S. PATENT DOCUMENTS

| | | | |
|---|---|---|---|
| 3,811,040 | 5/1974 | Weinfurt et al. | 128/699 X |
| 4,095,597 | 6/1978 | Hassler | 128/663 |
| 4,292,977 | 10/1981 | Krause et al. | 128/712 |
| 4,370,985 | 2/1983 | Takeichi et al. | 128/663 |
| 4,552,152 | 11/1985 | Tachita et al. | 128/663 |
| 4,630,612 | 12/1986 | Uchida et al. | 128/663 X |
| 4,660,565 | 4/1987 | Shirasoka | 128/663 X |
| 4,665,925 | 5/1987 | Miller | 128/663 |

FOREIGN PATENT DOCUMENTS 2156985 10/1985 United Kingdom ................ 128/660

Primary Examiner—Francis J. Jaworski
Attorney, Agent, or Firm—Darby & Darby

[57] ABSTRACT

The invention falls within the art field of electronic detection and measuring instruments for medical use. Connected to the audio output of a conventional Doppler device, the instrument disclosed processes the Doppler signal ($P_t$) and produces an output signal ($R_t$) in the form of a quantity per unit of time which is proportional to the radius of a circular cross-section equivalent in area to the effective cross-section of the blood vessel under examination. The instrument provides a video image of this 'relative' cross-section as well as producing a numerical read-out proportional to the maximum and the minimum radius of the relative cross-section which register during heartbeat.

9 Claims, 1 Drawing Sheet

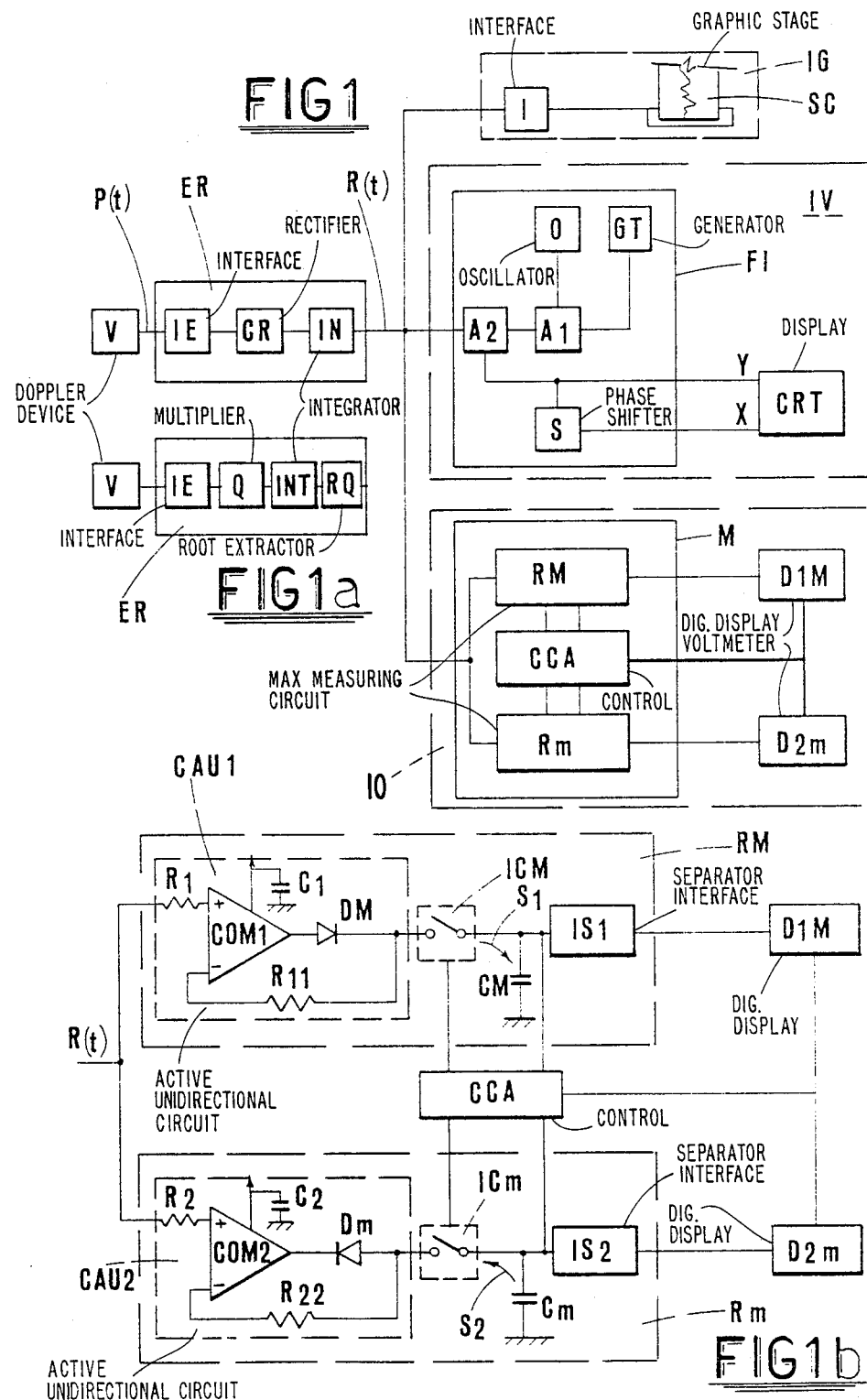

INSTRUMENT TO DETECT AND REPRESENT THE CROSS-SECTIONAL VARIATIONS OF A BLOOD VESSEL

BACKGROUND OF THE INVENTION

A person having skill in the art field which embraces electronic measuring apparatus for medical use will be aware that 'Doppler' type velocimeters have been commercially available for some time. Such devices detect velocity and direction of the circulation of blood through a given vessel by exploiting the Doppler effect, but cannot be considered measuring devices in the strict sense, as no calibration is possible.

The Doppler devices in question process a signal rebounding off corpuscles in the blood when the vessel under examination is invested with a beam of ultrasonic frequencies emitted by a transducer. The signal produced is suitably converted and fed into an electromechanical transducer in such a way as to generate an audible signal which, in current practice, serves to assess the hydraulic state of a blood vessel as an aid to diagnosis. Diagnosis of this conventional type makes no use of any remotely-reproduced visual indication of the cross-section of the blood vessel, or of variations in cross-section that occur from one moment to another; such visual information would be of considerable assistance however, and, correlated to the acoustic signal, could provide a visual representation of the hydraulic behavior of an artery or a vein.

The object of the invention disclosed herein is to provide an instrument which, by utilizing the audio output signal from a Doppler velocimeter, provides:

an acoustic signal processed in such a way as to enhance the quality of the information to be interpreted;

a circular cross-section representation of 'relative' changes with time of the effective cross-section of a column of blood through a blood vessel under examination, and of variation in the cross-section during heartbeat;

a proportional numerical read-out of the maximum and the minimum radius of the cross-section representation during heartbeat;

the facility of link-up to a printer or recorder that will document variations in radius of the relative cross-section over a given period of time.

SUMMARY OF THE INVENTION

The stated object is realized by adoption of the instrument as disclosed and claimed herein; such an instrument is designed for connection to a conventional Doppler device of the type used to detect velocity of the blood flowing through a vessel under examination, and comprises electronic circuitry such as will process a Doppler signal to the end of providing an output which is proportional to variations in radius per unit of time which register of a cross-section representation of the column of blood flowing through the blood vessel, and therefore reflects a positive value at any given moment.

In the instrument disclosed, variations per unit of time in the processed Doppler signal (which is proportional to the radius of the cross-section representation of the column of blood flowing through the blood vessel under examination) are displayed on a video screen by way of an image which reproduces the representation in circular format and monitors variations in its radius from one instant to the next.

The instrument provides a numerical read-out that is proportional to maximum and minimum levels of the proportional signal reflecting the radius of the representation, and further provides the option of link-up to a peripheral device which will print out or otherwise graphically record variations per unit of time occurring in the numerical read-out of the radius of the relative cross-section.

It will be appreciated from the foregoing that the novelty inherent in the invention, the concept of which will become clear from the specification, is that of measuring and displaying the content of a Doppler velocimeter output signal in a wholly original and singularly advantageous fashion.

Exploiting the signal provided by a Doppler device, and working from the results given by algorithmic calculation of the strength of a signal which (according to a given mathematical formula) matches the Doppler signal produced by the velocimeter employed, electronic circuitry may be designed such as will produce a signal strictly proportional to the variations per unit of time in radius of the blood vessel cross-section representation. Such a signal can then be exploited in embodying electronic circuitry that will provide an optical source both for projection of a moment-by-moment video image of the relative cross-section and produce a numerical read-out representing the maximum and minimum radius measurements of such a cross-section representation, which can also be recorded on paper. The facility of measuring maximum and minimum radial dimensions of the blood vessel further allows of obtaining an independent parameter reflecting the depth of the vessel, since the ratio between maximum radius and minimum radius of the vessel provides a diagnostic parameter of special importance, namely, elasticity of the vessel.

It will be observed that, having compiled a table of typical values indicating maximum cross-section (a measurement which must necessarily remain non-absolute) and elasticity of the various blood vessels in the human body, it becomes possible to pin-point any pathological condition immediately.

BRIEF DESCRIPTION OF THE DRAWINGS

The invention will now be described in detail, by way of example, with the aid of the accompanying drawings, in which:

FIG. 1 is a block diagram of the instrument to which the invention relates;

FIG. 1a illustrates an alternative embodiment of the electronic circuitry which produces a processed output signal proportional to the radius of the relative cross-section of a blood vessel;

FIG. 1b is a detailed diagram of the stage providing read-out of the maximum and minimum levels of the signal produced by circuitry as shown in FIG. 1.

DESCRIPTION OF THE PREFERRED EMBODIMENTS

Before passing on to a detailed description of the electronic circuitry making up the instrument disclosed herein, an exposition must be given of the basic concept upon which practical embodiment of the invention idea is made possible.

The output signal provided by a Doppler type detection device is the sum of constituents deriving from those single particles present within the blood vessel under examination. Clearly enough, therefore, a variation in strength of the signal will reflect a corresponding variation in the number of corpuscles invested with ultrasonic radiation emitted by the Doppler device, hence variation in the cross-section of the column of blood flowing through the vessel. It follows that, in order to detect the variation in cross-section of a blood vessel from which a Doppler signal is generated, an accurate estimation must be made of the short-term variation in strength of the signal received, and the errors inherent in estimation minimized by an appropriate choice of sampling frequency; in other words, a suitable time lapse must be selected for integration, as well as a suitable integrating medium, as will become clear in due course. An estimation thus performed, where account is taken of errors deriving from system noise, and process-related errors are kept within reasonable limits, can be referred direct to the cross-section of the blood vessel. Working, therefore, from the commonly accepted theory that concentration of particles in the blood remains unaltered across the time lapse necessary for a conventional Doppler analysis, the instrument disclosed herein is able to provide the user with a quantity that is proportional to the cross-section of the vessel under examination, and to do so independently of the velocity of the flow of blood therethrough. Needless to say, it is not the physical shape of a cross-section invested with ultrasonic radiation that such a method produces, but rather, the equivalent area effectively circumscribed; accordingly, the cross-section of the blood vessel will appear on the monitor screen in circular format, regardless of the shape it may exhibit in reality.

Whilst the prior art embraces different instruments that employ Doppler effect in providing an indication either of mean velocity, or of distribution of velocities, through a blood vessel, readings relating to the cross-section of blood vessels are obtained by other methods, such as angiography or sounding. It is with the precise object of filling this gap in the art field that the instrument disclosed has been developed; such an instrument can be linked up to conventional Doppler devices, whether designed for one-way or for reversible operation, and provides the user with a quantity, namely, the cross-section representation of a column of blood through the blood vessel under examination, from which to gain an accurate indication of the blood vessel's elasticity.

A person skilled in the art will be aware from existing literature that a Doppler signal produced by ultrasonic detection may be likened to zero mean and non-stationary gaussian noise superimposed on zero mean and stationary gaussian noise (thermal noise). Thus, in designing a processing method which will detect the cross-section representation referred to in the foregoing, the initial step is to compose a mathematical formula of the Doppler signal; this accomplished, a system for isolation of the short-term strength of the signal may be established.

In the case of the invention, the mathematical formula selected is multiplicative, and may be represented by the following equation:

$$s_t = \sqrt{I_t} n_t$$

where $I_t$ is the quantity to be estimated (short-term signal strength), $n_t$ represents stationary gaussian noise with zero mean and unitary variance, and $s_t$ is the Doppler signal.

The strength $P_t$ of the signal $s_t$, which is determined at the outset, calculated on successive strings of signal information each of T seconds duration (hence 'short-term strength', with $T < +\infty$), is given by the conventional equation.

$$P_t = \frac{1}{2T} \cdot \int_{-T}^{T} s^2(t - \alpha) d\alpha$$

The mathematical formula produced by such an equation leads to an electronic circuit design consisting substantially of a multiplier circuit Q that produces the square of its input, followed by an integrator circuit INT.

Basically, the multiplier cascades into the integrator, which totals components of the signal $s_t$ received within a preset time lapse T. In the case of the invention, it becomes necessary to perform an analysis by way of which to arrive at the optimum integration time, this being dependent upon two opposed requirements.

The first such requirement is that the time lapse T must be sufficiently brief to allow the instrument to follow any abrupt variations in short-term signal strength.

The second and opposite requirement is that the time lapse T must be sufficiently long in order to allow the instrument to average out and thus compensate fluctuations occurring over a given period of time—i.e. the result of statistical fluctuations in signal strength rather than the abrupt variations mentioned above.

Given that the quantity which must be known to the group of circuits that follow the multiplier and integrator circuits is simply the radius of the relative cross-section of the vessel, and that the output from the integrator circuit INT is proportional to short-term signal strength, hence to the cross-section representation of the vessel in question, it will suffice to compute the square root of such an output in order to produce a signal proportional to the radius of the relative cross-section generated. Accordingly, the integrator circuit INT will cascade into a further circuit, denoted RQ, the function of which substantially is to calculate the square root of the input signal it receives.

It will be observed that an interface IE is included between the Doppler output and the input of the multiplier circuit Q; this serves to adapt and filter the signal $P_t$ produced by the Doppler device. The entire stage comprising the interface IE, and the multiplier, integrator and root-division circuits Q, INT and RQ, is denoted ER in FIG. 1a.

The full impact of the idea claimed herein becomes evident when one observes that circuitry is provided downstream of the ER stage that will produce an image of the cross-section representation of the vessel on a video screen, the cross-section appearing as a solid circle the area of which is proportional to the area effectively calculated. To enable putting such a circular image together, the radius of the relative cross-section must be a known quantity, and this is proportional to the square root of the output supplied by the Doppler device—i.e., of the strength of the signal $P_t$.

It will be noted at this juncture, that a quantity $R_t$ proportional to the square root of the signal $P_t$ can also be isolated to advantage, given the gaussian conditions aforementioned, utilizing a stage of circuitry consisting simply of an interface IE identical to the first-mentioned, followed by a rectifier CR which cascades in its turn into an integrator IN. This is the arrangement that is adopted in the embodiment of the instrument as illustrated in FIG. 1.

Written documentation, computer simulations, and experiments conducted in vivo et in vitro have shown that the optimum integration time lapse T will be something between 50 and 300 msec, a fact likewise demonstrable by results obtained from analysis which are not included here in the interests of brevity.

With reference to FIG. 1, in addition to the Doppler device and the ER stage which produces the output signal denoted $R_t$, the instrument to which the invention relates also comprises a set of three visual information stages denoted IG, IV and IO.

The stage denoted IG produces a graphic representation of the signal $R_t$ in relation to time, and comprises an interface T, downstream of the ER stage, and a printer or recorder SC.

TV denotes a stage that gives a visual representation of the cross-section of a blood vessel under examination, and incorporates image-forming circuitry consisting substantially of a modulating system in which the carrier component is generated by an oscillator O and the modulating component by a generator GT. The carrier is suitably amplified by a first amplifier A1 controlled by the generator GT. The output from the amplifier A1, which is amplitude-modulated, is fed into a second amplifier A2 controlled by the ER stage, that is, by the processed input signal $R_t$, in order that maximum and minimum levels of the output signal provided by the second amplifier A2 will be amplitude-modulated in turn, according to the characteristic of the signal $R_t$. The output signal of this amplifier A2 is relayed direct to, say, the vertical deflection plates Y of a cathode ray tube, or CRT, whereas the horizontal deflection plates X of the same CRT are in receipt of the same A2 output phased through 90° by a shift network S. In this way one is able to create what the naked eye observes as a solid cross-section on the screen of the CRT the radius of which will vary commensurately with variations in the strength of the processed signal $R_t$.

A clearer understanding of the image-forming circuitry FI thus embodied will emerge from the following points.

A person skilled in the art will known that the application of a pair of sine wave input phased through 90° to the X and Y deflection plates of a cathode ray tube occasions movement of the electron beam through a circumference in a time equal to the period of the sinusoidal generators. By varying the amplitude of such waveforms, one obtains circumferences of differing radius; moreover, by varying the waveform from zero to a given maximum amplitude in continuous fashion, and at sufficiently high speed, the visual effect produced on the screen will be that of a solid circle of radius equal to the aforementioned maximum amplitude. In effect, the electron beam describes an Archimedes' spiral, and when the number of such spirals completed per unit of time is equal to or greater than the maximum number singly discernable by the naked eye, due to the retina's being permanently stimulated by the images, then one has a stable image.

Image-forming circuitry FI according to the invention exploits the visual effect thus described. Sine waves of equal amplitude are generated by the oscillator O, their amplitude being varied by the modulating influence of the generator GT, in such a way as to produce a cross-section on the CRT screen that appears solid to the naked eye. Given that the radius of such a cross-section varies in proportion to the strength of the input signal $R_t$, the second amplifier A2 must be controlled by the signal $R_t$ itself. Thus, one obtains an cross-sectional image of the blood vessel that is solid, and that varies in radius commensurately with the signal information supplied.

The necessity exists for a marked accentuation of the outermost part of the cross-section that appears on the screen, and to this end the invention proposes increasing luminous intensity at the edge of the circumference projected. This can be achieved by causing the electron beam to describe the outer circumference a given number of times before moving into the Archimedes' spiral, and is implemented in practice by providing the modulating output from the generator GT with trapezoidal or other similar waveform.

The stage denoted IO comprises circuitry M consisting substantially of two circuits RM and Rm for measurement of the maximum and mimimum strength, respectively, of the signal $R_t$. The two measurement circuits connect with relative digital display volt-meters D1M and D2m, and these four components are all governed by a control, denoted CCA, that resets the RM and Rm circuits following each sampling, and will memorize the results of one such sampling for a given length of time, at the discretion of the user.

More precisely, the RM circuit comprises an active unidirectional circuit CAU1 which, enabled by a solid state switch ICM forming part of the control (CCA), charges a capacitor CM by way of a diode DM, that is, in the direction denoted S1 in FIG. 1b, to the maximum measured value. The value thus produced is relayed through a separator interface IS1 to the relative display D1M.

When the ICM switch contacts are open, the capacitor CM can discharge by way of the CCA control in readiness for the next sampling cycle; with the ICM switch contacts closed, the capacitor CM clearly will recharge commensurately with the maximum level of the signal $R_t$ as supplied by the unidirectional circuit CAU1.

The circuit denoted Rm is embodied substantially in the same way as that denoted RM, comprising an active unidirectional circuit CAU2 which, enabled by a relative switch ICm forming part of the control (CCA) and operated synchronously with the switch ICM first mentioned, discharges a relative capacitor Cm by way of a diode Dm the direction of which is reversed in relation to the diode DM first mentioned. This capacitor Cm is charged at a positive potential greater than any minimum level of the signal $R_t$, by way of the control circuit CCA; thus, with the ICm switch contacts open, the capacitor Cm is charged by the control CCA, and when the ICm switch contacts close, the capacitor Cm discharges via the diode Dm, that is, in the direction denoted S2 in FIG. 1b. The minimum level of the signal $R_t$ is relayed to the relative display D2m through a respective separation interface IS2 identical in all respects to the first mentioned. Clearly, the charge into capacitor Cm is equivalent to the discharge from capacitor CM, and the right conditions are thus created for each fresh sampling cycle.

The numerical value read out by the two displays D1M and D2m can be memorized for a given space of time at the discretion of the user, utilizing a signal relayed from the control circuit CCA (clearly illustrated in FIG. 1b).

The two active directional circuits CAU1 and CAU2 may be described as current pumps, by reason of the charge/discharge roles they perform in conjunction with their respective capacitors CM and Cm. In addition to the diode DM (see FIG. 1b), circuit CAU1 further incorporates an operational amplifier COM1, resistors R1 and R11, and a polarity capacitor C1. Circuit CAU2 comprises an identical package of components—viz, operational amplifier COM2, resistors R2 and R22, polarity capacitor C2, and diode Dm.

Needless to say, an instrument as disclosed herein might be embodied using differently arranged electronic circuitry whilst remaining equivalent in terms of the art; such variants fall likewise within the scope of the fundamental concept claimed below.

What is claimed:

1. An instrument for detection of vessel blood velocity and display of a circular cross-section representation of relative changes with time of the effective cross-section of a column of blood through a blood vessel under examination, comprising:

a Doppler means for detecting velocity of the blood flowing through the vessel under examination as a function of time and for providing a Doppler output signal s(t) representative thereof;

electronic means for processing the said Doppler output signal s(t) and for providing as a function of said time t an output signal R(t) derived from said Doppler output signal s(t) without anatomic measurement, which is proportional to the variations in the radius of said circular cross-section representation of the column of blood flowing through the blood vessel and which reflects a positive value at any given moment; and means responsive to the output signal R(t) for displaying said circular cross-section representation such that changes with time of R(t) are represented by equivalent changes in the radius of said representation.

2. The instrument according to claim 1, wherein said means for displaying said circular cross-section representation comprise:

means for providing graphic documentation of the signal R(t) with respect to time;

means for providing an image of the circular cross-section representation of the blood vessel examined; and means for producing a read-out of the maximum and minimum measurements of the radius of said representation.

3. The instrument according to claim 2, wherein said means for providing graphic documentation of the processed signal R(t) comprises an interface circuit responsive to said signal R(t), the electronic processing means and a peripheral means responsive to said interface for printing or recording on paper.

4. The instrument according to claim 2, wherein the means for providing an image of said circular cross-section representation of the blood vessel examined comprises an image forming circuit including a modulating system whereby a carrier is generated by an oscillator and a generator for producing modulation, wherein the carrier is amplified by a first amplifier controlled by said generator so as to produce an amplitude-modulated signal, the amplitude modulated signal being coupled to a second amplifier controlled by said electronic processing means so that the maximum and minimum levels of the output signal of said second amplifier is amplitude-modulated according to the characteristic of the processed input signal R(t), and wherein the output signal from the second amplifier is applied to the vertical deflection plates of a cathode ray tube, the horizontal plates of the same CRT being in receipt of the same signal phase shifted by 90° by a phase shift network so as to create an image on the screen of the CRT observed by the naked eye as a solid circle, the radius of which varies commensurately with variations of the processed input signal R(t).

5. The instrument according to claim 4, wherein the waveform modulation produced by the generator is substantially trapezoidal.

6. The instrument as in claim 2, wherein said means for producing read-out of maximum and minimum levels of the processed input signal R(t) comprises a circuit including measurement circuit means and a pair of displays, both such displays being governed by control means for resetting the measurement circuit means following each sampling, and for memorizing the results of one such sampling for a given length of time, at the discretion of the user.

7. The instrument according to claim 6, the measurement circuit means respectively comprising a first active unidirectional circuit including a solid state switch for enabling said circuit, said switch forming part of the control means for charging a downstream capacitor (CM) by way of a diode (DM) to the maximum measured value, which value is then relayed through a separator interface to the relative display (D1M), wherein the open state of the switch discharges the capacitor via the control in readiness for a fresh sampling cycle, and a second active unidirectional circuit having a switch (ICm) for enabling said circuit, said switch forming part of the control means and operating synchronously with said solid state switch (ICM) for discharging a downstream capacitor (Cm) by way of a diode (Dm), the direction of which is reversed in relation to said diode (DM) to the minimum measured value, which is then relayed through a separation interface to the respective display (D2m), wherein the capacitor (Cm) is charged at a positive potential via the control means and wherein the open state of the switch (ICm) charges the capacitor (Cm) by way of the control in readiness for a fresh sampling cycle.

8. The instrument according to claim 1, wherein said electronic means for processing includes a cascade of stages comprising:

an interface circuit, having an output, that adapts and filters the Doppler signal s(t);

a multiplier circuit, having an output and responsive to the output of said interface circuit, the function of which substantially is to produce the square of the input signal it receives;

an integrator circuit having an output and responsive to the output of said multiplier circuit; and a circuit, responsive to said integrator output, the function of which substantially is to find the square root of the input signal it receives.

9. The instrument according to claim 1, wherein said electronic means for processing includes a cascade of stages comprising:

an interface, having an output, that adapts and filters the Doppler signal s(t);

a rectifier circuit, having an output and responsive to the output of said interface, the function of which substantially is to rectify the Doppler signal s(t); and an integrator circuit responsive to the output of said rectifier circuit.

* * * * *